United States Patent [19]
Massaro

[11] Patent Number: 5,085,208
[45] Date of Patent: Feb. 4, 1992

[54] METHOD OF MASSAGE AND PREPARATION THEREFOR

[76] Inventor: Angelo S. Massaro, 549 Belgrove Dr., Kearny, N.J. 07032

[21] Appl. No.: 639,115

[22] Filed: Jan. 7, 1991

[51] Int. Cl.$^5$ .................... A61H 7/00; A01N 65/00
[52] U.S. Cl. .................... 128/67; 424/195.1; 128/32
[58] Field of Search .............. 424/195.1, 45, 59; 128/67

[56] References Cited

U.S. PATENT DOCUMENTS

| | | | |
|---|---|---|---|
| 137,624 | 4/1873 | Rose | 424/195.1 |
| 139,045 | 5/1873 | Conzelman | 424/195.1 |
| 397,192 | 2/1889 | Lindgren | 424/195.1 |

Primary Examiner—Robert A. Hafer
Assistant Examiner—Brian E. Hanlon
Attorney, Agent, or Firm—Levonna Herzog

[57] ABSTRACT

A method of massage using a new preparation which contains lemon oil and lemon juice is disclosed. The new preparation is effective for relief of aches and pains, especially in the joint areas.

17 Claims, No Drawings

METHOD OF MASSAGE AND PREPARATION THEREFOR

BACKGROUND OF THE INVENTION

This invention concerns a method and preparation useful for the relief of muscular aches and pains and pains in joint areas. More particularly this invention is directed to a method of body massage using a preparation which is effective to reduce pain of aching muscles and joints and also pain associated with arthritis and to the preparation used therefor.

Many people suffer from muscle and joint pain, especially after exercise. Also, muscle and joint pain, as well as pain associated with arthritis seem to increase with age. While body massage can be helpful in relieving such pain, the relief is often short-lived.

Products are on the market which purport to relieve arthritis pain, muscle aches and the like. However, these products generally contain medicaments which can be harmful, are expensive or can be irritating if used often.

Therefore, a preparation which is non-toxic and provides longer acting relief without use of pain killing and possibly harmful medicaments would provide important advantages over currently available products.

SUMMARY OF THE INVENTION

An object of the invention is to provide a method of massage using a preparation which enhances the effects of the massage.

Another object of the invention is to provide a method for the relief of body aches and pains by a a low cost, non-toxic preparation which contains no synthetic pain killing medicaments.

A further object of the invention is the provision of a method for relieving muscle aches and pains, pain in the joint areas and pain associated with arthritis by a simple, easy to use method.

Still another object of the invention is to provide a non-toxic, low cost preparation for application to the body which is effective for relief of muscle and joint pains.

These and other objects of the invention are attained by the method and preparation disclosed below.

I have discovered that external application to an area of the body suffering from muscle or joint pain of a preparation comprising lemon oil in an amount of about 10-15% by volume and lemon juice, which may be reconstituted from lemon juice concentrate, in an amount of about 85-90% by volume, and massaging the area is effective to reduce or relieve the pain in the muscle or joint.

DESCRIPTION OF THE INVENTION

Use of the preparation of the invention as a smoothing lotion during a body massage has been found to greatly enhance the effects of the massage.

The preparation of the invention can be applied safely to any external part. The astringency of the lemon juice may cause minor irritation to abrasions and open wounds; therefore, application to such areas should be avoided. However, if such contact should occur, flushing with water will correct the problem immediately.

External application of the preparation of the invention provides relief from the effects of arthritic inflammation and is useful as an aid for muscle relaxation and relief of muscular aches and joint pain. For people suffering from muscle debilitation due to aging, application of the preparation of the invention with mild rubbing allows easier motion and is an aid in carrying out normal activities of walking, bending etc. It has been found that application of the preparation of the invention is particularly beneficial when applied to the knee area.

The preparation can be homogenized and dispensed from a spray bottle. Also, or alternatively, an emulsifying agent can be included in the preparation of the invention in an amount effective to provide an emulsion, and the resultant emulsion can be dispensed from any type of ordinarily used container. Any non-toxic water-oil emulsifier can be used and among these, gums, such as arabic, xanthan and tragacanth gums have been found to be suitable emulsifiers. Arabic gum is preferred due to its low cost and may be present in the preparation of the invention in an amount of about 1.5 to 4 parts by weight, per 100 parts by weight of the preparation.

As the lemon oil, natural lemon oil, such as that obtained from lemon skin and/or lemon seeds is preferred. Suitable lemon oil can be purchased, for example, from Lorann Oils, Inc., Lansing, Mich. and Bickford Laboratories, Akron, Ohio.

A preferable preparation of the invention contains lemon oil in an amount of about 12.5% by volume and lemon juice concentrate in an amount of about 20% by volume. This preparation can be diluted with up to about 67.5% by volume of water. The solution preferably contains a perservative, such as sodium benzoate and/or sodium bisulfite. Natural strength lemon juice from concentrate, such as that available in most food markets, or freshly squeezed lemon juice can be substituted for the lemon juice concentrate and water.

The invention is further exemplified by the following example, which illustrates the best mode currently contemplated for carrying out the invention, but which must not be construed as limiting the invention in any manner.

EXAMPLE

Twenty-five ml of lemon oil obtained from Bickford Laboratories are mixed with 40 ml of lemon juice concentrate (Shoprite brand) which contains 0.1% by weight of sodium benzoate and 0.05% by weight of sodium bisulfite preservatives, 135 ml of filtered water and 3.2 g of gum arabic.

The resultant emulsion is readily for use and can be packaged in the desired manner. For example, the preparation of the invention can be absorbed (with or without the emulsifier) in towels and the saturated towels can then be sealed in an airtight package. The preparation of the invention, without the addition of water, can be sealed in concentrated form in quick melting pellets or capsules useful for bath water. In homogenized or emulsion form, the preparation of the invention can be packed in a container equipped with spraying means.

For persons suffering from muscle aches and pains, particularly aches and pains associated with aging and with arthritis, it is recommended that the preparation of the invention be applied daily, with light massage to the affected areas upon rising and when retiring.

What I desire to claim and protect by Letters Patent is:

1. A method of body massage useful for providing relief from muscular aches and pains associated with joints comprising the following steps applying a preparation to the pain affected area containing lemon oil in an amount of about 10-15% by volume and lemon juice in an amount of 85–90% by volume and massaging the pain affected area.

2. The method according to claim 1, in which the preparation contains about 12.5% by volume of lemon oil, about 20% by volume of lemon juice concentrate and about 67.5% water.

3. The method according to claim 1, in which the preparation is in homogenized form.

4. The method according to claim 1, in which the preparation is absorbed in a towel which is in an air tight package and the preparation is applied with the aid of the towel.

5. The method according to claim 1, in which the preparation is in the form of an emulsion and contains a non-toxic water-oil emulsifier in an amount effective to emulsify the lemon oil and lemon juice.

6. The method according to claim 1, in which the preparation is in the form of an emulsion and contains gum arabic in an amount of about 1.5 to 3.5 parts by weight per 100 parts by weight of the preparation.

7. The method according to claim 1, in which the preparation is applied to the area of the knee joints.

8. A preparation useful for enhancing body massage and for relieving muscle aches and joint pains comprising lemon oil in an amount of about 10–15% by volume and lemon juice in an amount of 85–90% by volume.

9. The preparation according to claim 8 which contains about 12.5% by volume of lemon oil, about 20% by volume of lemon juice concentrate and about 67.5% water.

10. The preparation according to claim 8 which is in homogenized form.

11. The preparation according to claim 8, in which the preparation is absorbed in a towel which is in an air tight package 12. The preparation according to claim 8 which is in the form of an emulsion and contains a non-toxic water-oil emulsifier in an amount effective to emulsify the lemon oil and lemon juice.

13. The preparation according to claim 8, which is in the form of an emulsion and contains gum arabic in an amount of about 1.5 to 3.5 parts by weight per 100 parts by weight of the preparation.

14. The method according to claim 1, in which the preparation applied comprises as essential active ingredients lemon oil in an amount of 10–15% by volume and lemon juice in an amount of 85–90% by volume.

15. The method according to claim 1, in which the preparation applied essentially consists of lemon oil in an amount of 10–15% by volume and lemon juice in an amount of 85–90% by volume.

16. The preparation according to claim 8 which comprises as essential active ingredients lemon oil in an amount of 10–15% by volume and lemon juice in an amount of 85–90% by volume.

17. The preparation according to claim 8 which essentially consists of lemon oil in an amount of 10–15% by volume and lemon juice in an amount of 85–90% by volume.

* * * * *